United States Patent
Choi et al.

(10) Patent No.: US 10,209,220 B2
(45) Date of Patent: Feb. 19, 2019

(54) APPARATUS FOR MEASURING ION MOBILITY OF HARMFUL MATERIAL AND REFERENCE DATA OBTAINING METHOD OF THE SAME

(71) Applicant: Korea Basic Science Institute, Cheongju-si, Chungcheongbuk-do (KR)

(72) Inventors: Myoung Choul Choi, Cheongju-si (KR); Jeong-Hoon Kang, Pohang-si (KR); Jung-Hwan Kim, Pyeongtaek-si (KR)

(73) Assignee: Korea Basic Science Institute, Cheongju-si, Chungcheongbuk-do (KR)

( * ) Notice: Subject to any disclaimer, the term of this patent is extended or adjusted under 35 U.S.C. 154(b) by 0 days.

(21) Appl. No.: 15/323,317

(22) PCT Filed: Nov. 26, 2015

(86) PCT No.: PCT/KR2015/012767
§ 371 (c)(1),
(2) Date: Dec. 30, 2016

(87) PCT Pub. No.: WO2017/090792
PCT Pub. Date: Jun. 1, 2017

(65) Prior Publication Data
US 2018/0275098 A1   Sep. 27, 2018

(30) Foreign Application Priority Data
Nov. 26, 2015  (KR) .................. 10-2015-0166108

(51) Int. Cl.
*G01N 27/62*   (2006.01)
*H01J 49/16*   (2006.01)
(Continued)

(52) U.S. Cl.
CPC ........... *G01N 27/622* (2013.01); *G01N 27/64* (2013.01); *H01J 49/0036* (2013.01); *H01J 49/161* (2013.01)

(58) Field of Classification Search
USPC ......................................... 250/281, 282, 286
See application file for complete search history.

(56) References Cited

U.S. PATENT DOCUMENTS 5,701,009 A   12/1997   Griffiths et al.
6,495,823 B1  12/2002   Miller et al.
(Continued)

FOREIGN PATENT DOCUMENTS

JP   2007-192691   8/2007
KR   1996-0701362   2/1996
(Continued)

OTHER PUBLICATIONS

Hark Sang Kim et al , "Noise reduction of IMS signal using moving average filter", The Institute of Electronics Engineers of Korea, Nov. 1993, 922-925 (4 pages).
(Continued)

*Primary Examiner* — Kiet T Nguyen
(74) *Attorney, Agent, or Firm* — McAndrews, Held & Malloy, Ltd.

(57) ABSTRACT

Provided are an apparatus for measuring an ionic mobility of a harmful material and a reference data obtaining method thereof. The method includes obtaining a measurement signal by detecting a charge of an ion between electrodes, obtaining a noise signal by insulating the electrodes from the ion, aligning the noise signal with the measurement signal, removing a part of the measurement signal aligned with the noise signal, and calculating reference data from a remaining part of the measurement signal.

11 Claims, 7 Drawing Sheets

(51) Int. Cl.
*H01J 49/00* (2006.01)
*G01N 27/64* (2006.01)

(56) References Cited

U.S. PATENT DOCUMENTS

| | | |
|---|---|---|
| 7,714,278 B2 | 5/2010 | Boyle et al. |
| 8,044,343 B2 | 10/2011 | Arii et al. |
| 8,319,177 B2 | 11/2012 | Boyle et al. |
| 8,754,366 B2 | 6/2014 | Burchfield et al. |
| 2010/0258715 A1 | 10/2010 | Turner |
| 2016/0118234 A1* | 4/2016 | Covey .................. G01N 27/624 |
| | | 250/282 |

FOREIGN PATENT DOCUMENTS

| | | |
|---|---|---|
| KR | 2001-0060199 | 7/2001 |
| KR | 1110358 | 1/2006 |
| KR | 20070052774 | 5/2007 |
| KR | 20080111444 | 12/2008 |
| KR | 2010-0103624 | 9/2010 |
| KR | 20120086039 A | 8/2012 |

OTHER PUBLICATIONS

International Search Report dated Aug. 25, 2016 corresponding to International Application No. PCT/KR2015/012767.

* cited by examiner

APPARATUS FOR MEASURING ION MOBILITY OF HARMFUL MATERIAL AND REFERENCE DATA OBTAINING METHOD OF THE SAME

CROSS-REFERENCE TO RELATED APPLICATIONS/INCORPORATION BY REFERENCE

This application is a 371 of International Patent Application No. PCT/KR2015/012767, filed Nov. 26, 2015, entitled "APPARATUS FOR MEASURING ION MOBILITY OF HARMFUL MATERIAL AND REFERENCE DATA OBTAINING METHOD OF THE SAME", which claims priority to Korean Patent Application No. 10-2015-0166108, filed Nov. 26, 2015. The above-identified applications are hereby incorporated herein by reference in their entirety.

TECHNICAL FIELD

The present invention disclosed herein relates to a measurement apparatus and a signal obtaining method thereof, and more particularly, to an apparatus for measuring ionic mobility of a harmful material with an ability of photoionization and a reference data obtaining method of the same.

BACKGROUND ART

Harmful gas leakage accidents often occur in chemical plants. Harmful gas leakage may cause the loss of lives or serious accidents such as a fire. In industrial fields, detectors are almost necessarily used to detect a leakage of harmful gas. Furthermore, detectors may be used in various other fields such as nuclear, biological and chemical reconnaissance, measurement of air pollution, detection of harmful materials, etc. Accordingly, the demand for detectors is increasing. Detectors are being developed to satisfy the requirements of portability, ease of use, high sensitivity, and high optionality.

DISCLOSURE OF THE INVENTION

Technical Problem

Exemplary embodiments provides a harmful material ionic mobility measuring apparatus capable of detecting a noise.

Exemplary embodiments also provides a reference data obtaining method of a harmful material ionic mobility measuring apparatus for improving reliability.

Technical Solution

Exemplary embodiments of the inventive concept provides a reference data obtaining method for an ionic mobility measuring apparatus, including: obtaining a measurement signal by detecting a charge of an ion between electrodes; obtaining a noise signal by insulating the electrodes from the ion; aligning the noise signal with the measurement signal; removing a part of the measurement signal aligned with the noise signal; and calculating reference data from a remaining part of the measurement signal.

In exemplary embodiments of the inventive concept, an apparatus for measuring an ionic mobility of a harmful material includes: a chamber filled with a harmful material; a plurality of electrodes disposed in the chamber; a laser configured to irradiate a laser beam to the harmful material between the electrodes; a detector connected to the electrodes and detecting an ion of the harmful material ionized by the laser beam; and an ion filter disposed between the electrodes and insulating the ion from the electrodes so that the detector detects a noise of the ion through the ion filter.

Advantageous Effects

As described above, an ionic mobility measuring apparatus according to exemplary embodiments of the inventive concept may include an ion filter between electrodes. The ion filter may insulate ions of a harmful material from the electrodes. Not an ion current but a noise signal may be detected through a detector together with an ion signal. A control unit may calculate reference data from a measurement signal from which the noise signal has been removed. Therefore, the reference data obtaining method of the ion mobility measuring apparatus may improve the reliability.

MODE FOR CARRYING OUT THE INVENTION

Exemplary embodiments of the present invention will now be described in detail with reference to the accompanying drawings. The advantages and features of the present invention, and methods for achieving the advantages and features will be apparent from the embodiments described in detail below with reference to the accompanying drawings. Therefore, the present invention may be embodied in different forms and should not be construed as limited to the embodiments set forth herein. Rather, these embodiments are provided so that this disclosure will be thorough and complete, and will fully convey the scope of the present invention to those skilled in the art, and the present invention is only defined by the scope of the claims. Like reference numerals refer to like elements throughout.

The terminology used herein is not for delimiting the embodiments of the present invention but for describing the embodiments of the present invention. The terms of a singular form may include plural forms unless otherwise specified. It will be further understood that the terms "includes", "including", "comprises", and/or "comprising", when used in this description, specify the presence of stated elements, steps, operations, and/or components, but do not preclude the presence or addition of one or more other elements, steps, operations, and/or components. Furthermore, the terms such as a chamber, a thin film, and a coating may be construed as common terms used in the field of semiconductor and device. Reference numerals, which are presented in the order of description, are provided according to the embodiments and are thus not necessarily limited to the order.

Figure 1:
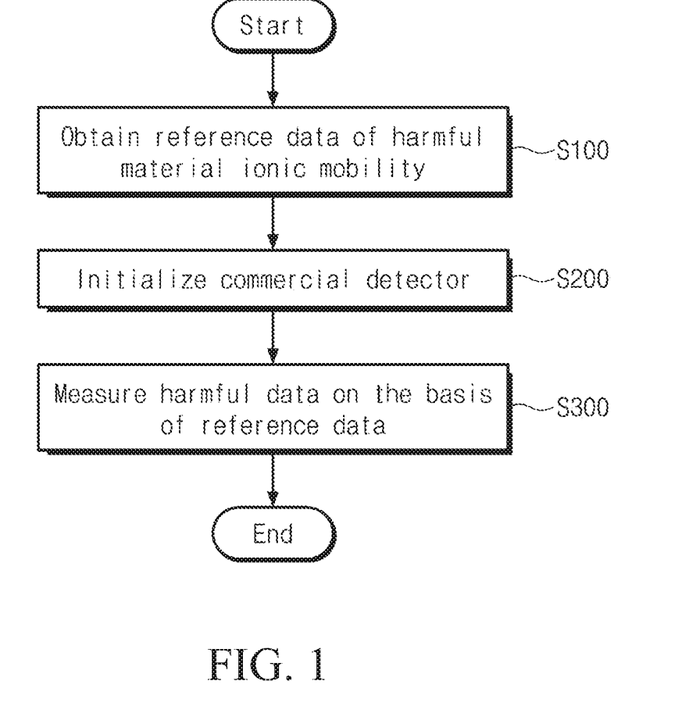
FIG. 1 is a flowchart illustrating a typical method for detecting a harmful material.

FIG. 1 illustrates a typical method for detecting a harmful material.

Referring to FIG. 1, the typical method for detecting a harmful material may include obtaining reference data (S100), initializing a commercial detector (S200), and measuring a harmful material (S300).

The obtaining reference data (S100) may include obtaining reference data of an ionic mobility of a harmful material. The harmful material may include a toxic material harmful to a human body. For example, the harmful material may include petrochemical elements of benzene, toluene, and xylene. Such harmful materials may have different values of ionic mobility according to the types thereof. The ionic mobility of a harmful material may be differently detected according to a measurement environment. For example, the ionic mobility may change according to a structure of a measurement electrode, a measurement frequency, a measurement waveform, and a measurement voltage. According to one example, the reference data may include data corresponding to the ionic mobility of a harmful material.

The initializing a commercial detector (S200) may include installing the reference data of the ionic mobility of a harmful material in a commercial detector. For example, the commercial detector may include a gas sensor, a gas detector, and a gas alarm. Accordingly, the commercial detector may be initialized by the reference data.

The measuring a harmful material (S300) may include detecting an indoor or outdoor harmful material using the commercial detector. The commercial detector may detect the type or concentration of a harmful material on the basis of the reference data. Therefore, the reference data may determine performance of the commercial detector. The reference data may be obtained from an apparatus for measuring ionic mobility of a harmful material.

Figure 2:
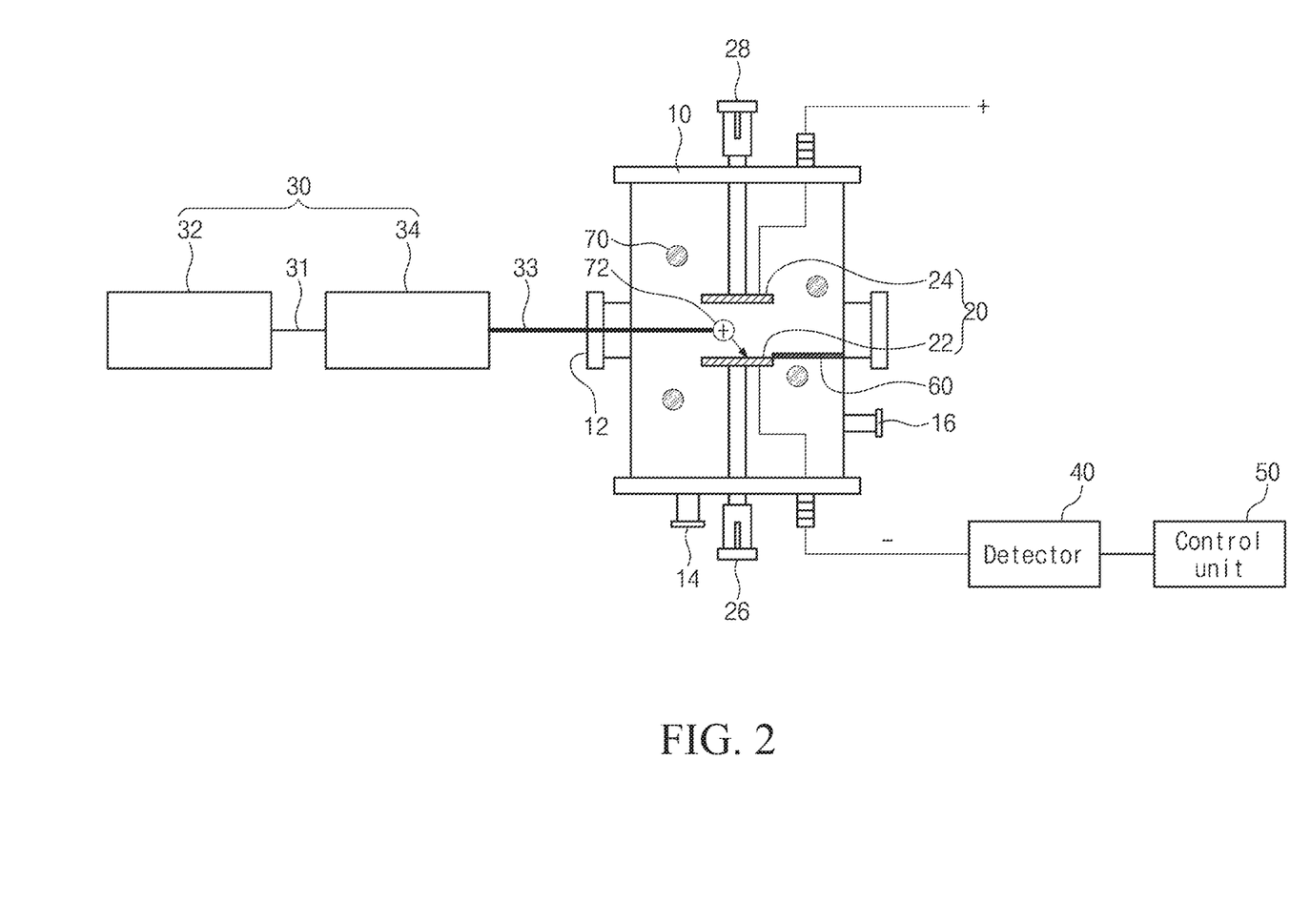
FIG. 2 is a diagram illustrating a harmful material ionic mobility measuring apparatus according to exemplary embodiments of the inventive concept.

FIG. 2 illustrates a harmful material ionic mobility measuring apparatus 100 according to exemplary embodiments of the inventive concept.

Referring to FIG. 2, the harmful material ionic mobility measuring apparatus 100 according to exemplary embodiments of the inventive concept may include a chamber 10, electrodes 20, a laser 30, a detector 40, a control unit 50, and an ion filter 60.

The chamber 10 may provide a space independent from the outside. The chamber 10 may have an atmospheric environment. Alternatively, the chamber 10 may be filled with a harmful material 70. For example, the chamber 10 may have view ports 12, a gas inlet 14, and an exhaust outlet 16. The view ports 12 may include a window of a sidewall of the chamber 10. The inside of the chamber 10 may be viewed through the view ports 12. Air or the harmful material 70 may be provided into the chamber 10 through the gas inlet 14. The air or the harmful material 70 introduced into the chamber 10 through the gas inlet 14 may be exhausted through the exhaust outlet 16. Although not illustrated, a gas supply unit may be connected to the gas inlet 14. The exhaust outlet 16 may be connected to a pump.

The electrodes 20 may be disposed in the chamber 10. According to one example, the electrodes 20 may include a lower electrode 22 and an upper electrode 24. The lower electrode 22 may be disposed on a lower rod 26 under the chamber 10. The upper electrode 24 may be disposed on the lower electrode 22. The upper electrode 24 may be connected to an upper rod 28. A distance between the lower electrode 22 and the upper electrode 24 may be adjusted by the lower rod 26 and the upper rod 28. The lower electrode 22 and the upper electrode 24 may have a potential difference. For example, the lower electrode 22 may be charged with a negative voltage. The upper electrode 24 may be charged with a positive voltage. The harmful material 70 may be provided between the lower electrode 22 and the upper electrode 24.

The laser 30 may be disposed outside the chamber 10. According to one example, the laser 30 may include a first laser 32 and a second laser 34. The first laser 32 may provide a pump light 31 to the second laser 34. For example, the first laser 32 may include an Nd-YAG laser. The pump light 31 may have a wavelength of about 1064 nm. The second laser 34 may include a dye laser. The second laser 34 may generate a laser beam 33 from the pump light 31. The laser beam 33 may have a wavelength of about 266 nm. The second laser 34 may provide the laser beam 33 between the lower electrode 22 and the upper electrode 24. The laser beam 33 may be provided into the chamber 10 through one of the view ports 12. The laser beam 33 may be provided to the harmful material 70 between the lower electrode 22 and the upper electrode 24. The harmful material 70 may be charged with an ion 72. The ion 72 may be a cation. The ion 72 may be captured by the lower electrode 22.

The detector 40 may be connected to the lower electrode 22. The detector 40 may detect a charge of the ion 72 through the lower electrode 22. The detector 40 may be connected to the control unit 50.

The control unit 50 may obtain the mobility of the ion 72 from a measurement signal of the detector 40. According to one example, the ionic mobility of the ion 72 may be a value obtained by dividing a drift distance of the ion 72 by a peak time of the measurement signal and a voltage V between the lower electrode 22 and the upper electrode 24. For example, the drift distance of the ion 72 may correspond to a distance between the laser beam 33 and the lower electrode 22. The distance between the laser beam 33 and the lower electrode 22 and the voltage V between the lower electrode 22 and the upper electrode 24 may be determined by a set value of the harmful material ionic mobility measuring apparatus 100. The peak time of the measurement signal may correspond to a peak time from an incident time point of the laser beam 33 to a time point at which the ion 72 is detected. The peak time of the measurement signal may change according to the type of the ion 72. That is, when the peak time of the measurement signal is obtained, the control unit 50 may calculate the reference data.

The ion filter 60 may be disposed in the chamber 10. The ion filter 60 may be disposed at an outer perimeter of the lower electrode 22 and the upper electrode 24 when detecting the ion 72. Alternatively, the ion filter 60 may be disposed outside the chamber 10.

Figure 3:
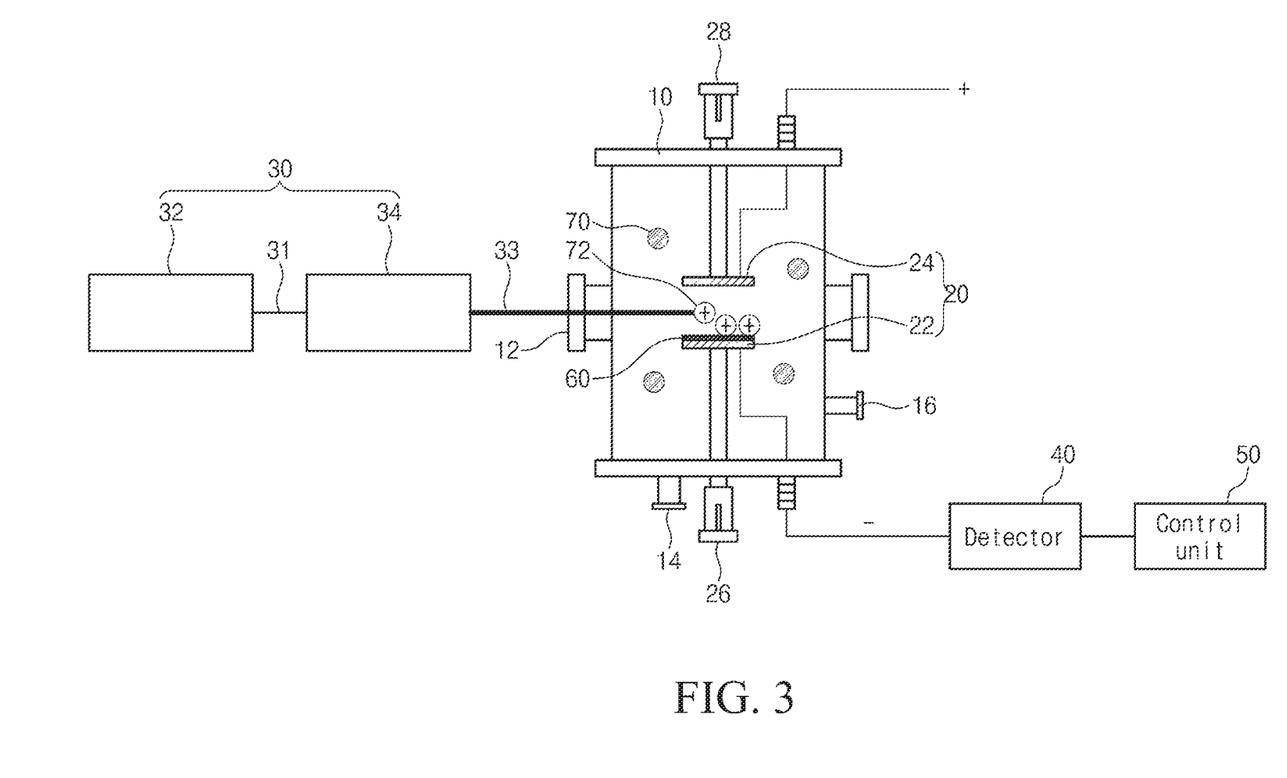
FIG. 3 is a diagram illustrating another example of the harmful material ionic mobility measuring apparatus of FIG. 2.

FIG. 3 illustrates another example of the harmful material ionic mobility measuring apparatus 100 of FIG. 2.

Referring to FIG. 3, the ion filter 60 may be disposed between the lower electrode 22 and the upper electrode 24 when detecting a noise of the measurement signal. According to one example, the ion filter 60 may be disposed between the laser beam 33 and the lower electrode 22. For example, the ion filter 60 may be disposed under the laser beam 33 and may contact onto the lower electrode 22. The ion filter 60 may insulate the lower electrode 22 from the ion 72. The chamber 10, the laser 30, the detector 40, and the control unit 50 may be configured in the same manner as described above with reference to FIG. 2.

Figure 4:
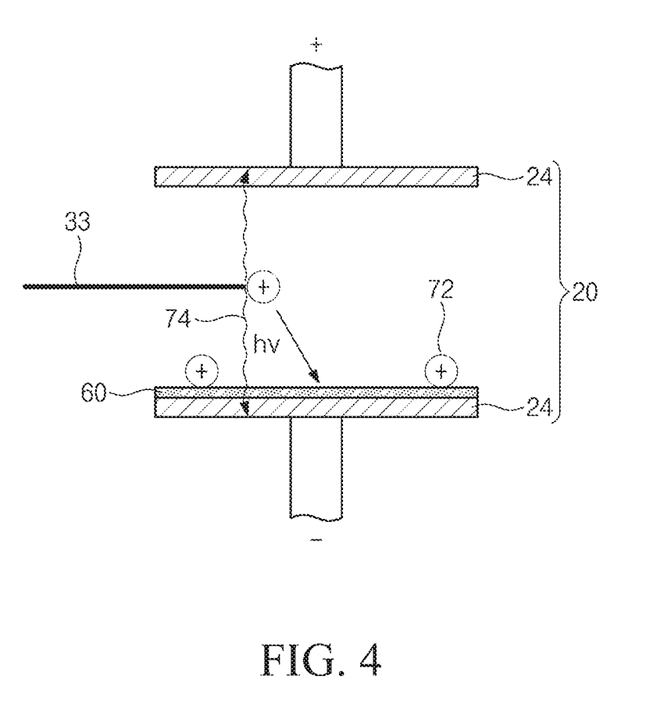
FIG. 4 is a diagram illustrating the electrodes and the ion filter of FIG. 3.

FIG. 4 illustrates the electrodes 20 and the ion filter 60 of FIG. 3.

Referring to FIG. 4, the ion filter 60 may transmit an ultraviolet light 74. According to one example, the ion filter 60 may include an ultraviolet transmission filter. For example, the ion filter 60 may include a monochromatic filter quartz or a monochromatic filter film. The ultraviolet light 74 may be generated when the laser beam 33 collides with the harmful material 70. The ultraviolet light 74 may be incident to the lower electrode 22 and the upper electrode 24. The ultraviolet light 74 may drop the voltage between the lower electrode 22 and the upper electrode 24 due to a photoelectric effect. The voltage drop may act as a noise of measurement of the ion 72. That is, the ultraviolet light 74 may be detected as a noise signal of the measurement signal of the ion 72.

Figure 5:
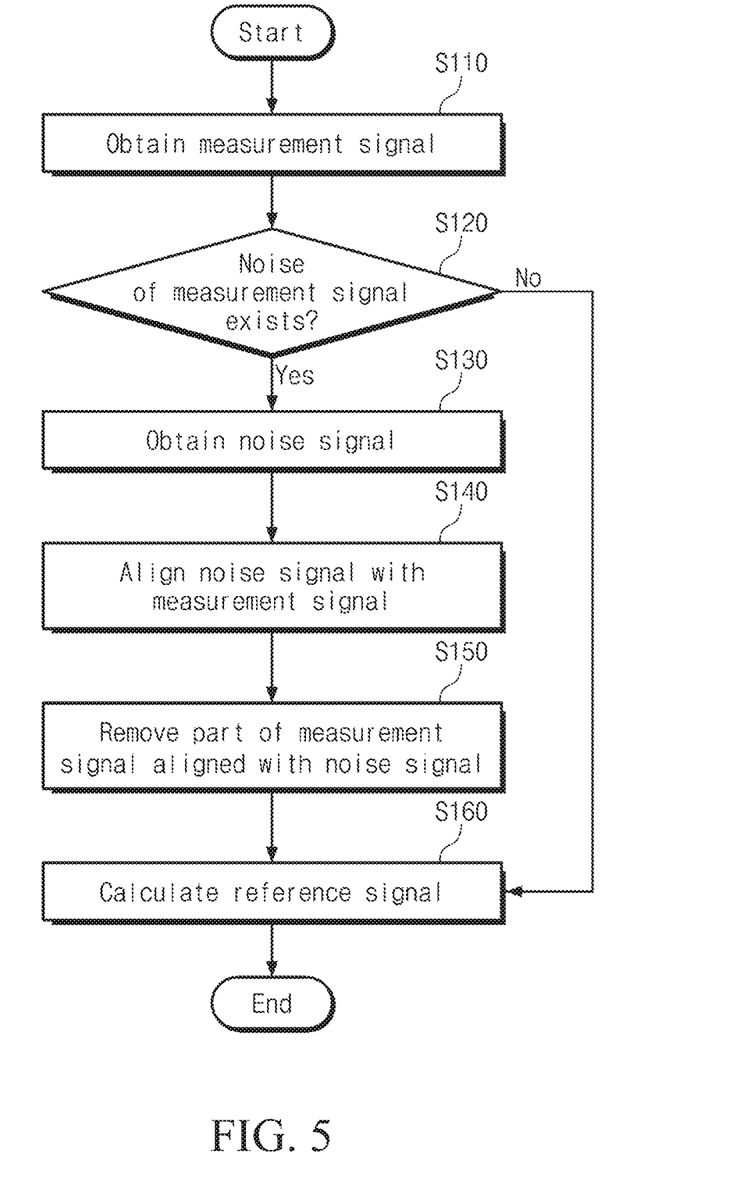
FIG. 5 is a flowchart illustrating an example of a reference data obtaining method for the harmful material ionic mobility measuring apparatus of FIG. 2.
Figure 6:
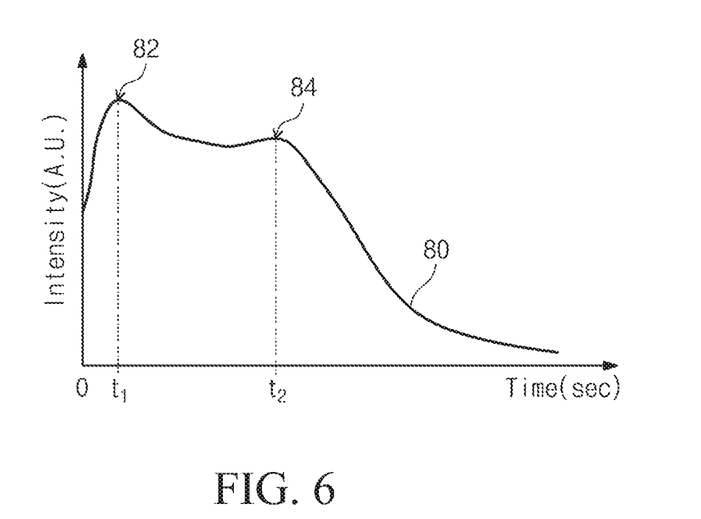
FIG. 6 is a graph illustrating a measurement signal detected by the detector of FIG. 2.

FIG. 5 illustrates an example of a reference data obtaining method for the harmful material ionic mobility measuring apparatus 100 of FIG. 2. FIG. 6 illustrates a measurement signal 80 detected by the detector 40 of FIG. 2.

Referring to FIGS. 5 and 6, the control unit 50 obtains the measurement signal 80 of the ion 72 through the detector 40 (S110). According to one example, the measurement signal 80 may have a first measurement peak 82 and a second measurement peak 84. The first measurement peak 82 may be detected at a first peak time $t_1$ from a start time point 0. The second measurement peak 84 may be detected at a second peak time $t_2$ after the first measurement peak 82.

Next, the control unit 50 determines whether there is a noise (S120). When the measurement signal 80 has a plurality of peaks, the control unit 50 may determine that a noise of the measurement signal 80 exists. In the case of FIG. 6, the control unit 50 may determine that a noise of the measurement signal 80 exists. On the contrary, when the measurement signal 80 has one peak, the control unit 50 may determine that there is no noise of the measurement signal 80.

Figure 7:
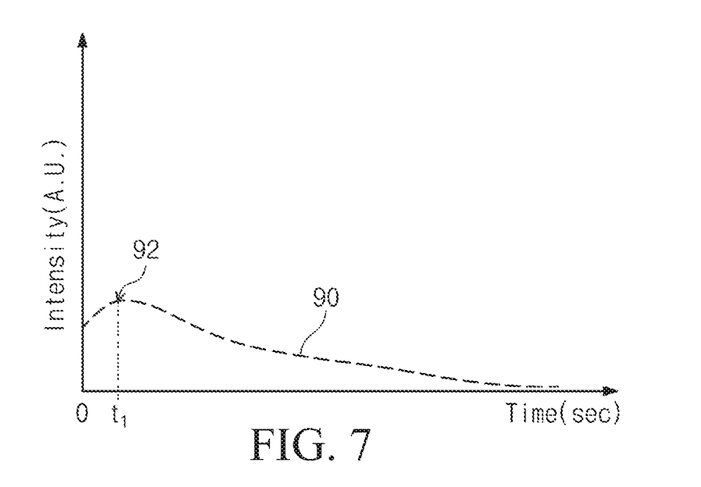
FIG. 7 is a graph illustrating a noise signal detected by the detector of FIG. 2.

FIG. 7 illustrates a noise signal 90 detected by the detector 40 of FIG. 2.

Referring to FIGS. 5 and 7, the control unit 50 obtains the noise signal 90 (S130). According to one example, the noise signal 90 may have a noise peak 92. The noise peak 92 may be detected at the first peak time $t_1$ from the start time point 0.

Figure 8:
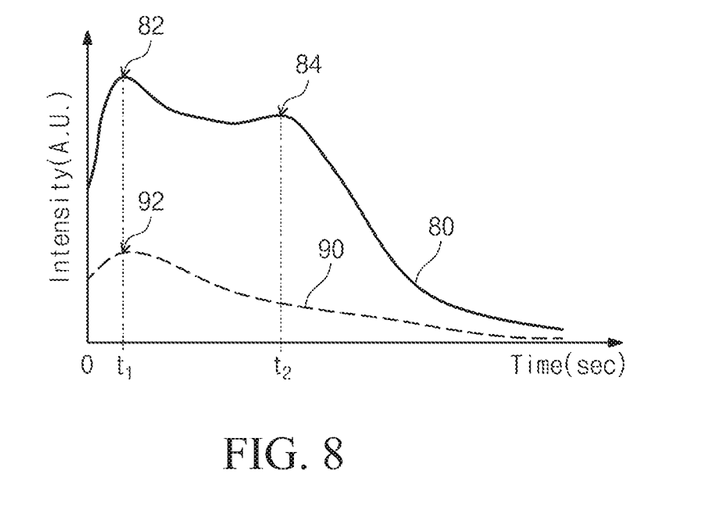
FIG. 8 is a graph illustrating the measurement signal and the noise signal of FIGS. 6 and 7.

FIG. 8 illustrates the measurement signal 80 and the noise signal 90 of FIGS. 6 and 7.

Referring to FIGS. 5 and 8, when the noise signal 90 exists, the control unit 50 aligns the noise signal 90 with the measurement signal 80 (S140). The first measurement peak 82 may be aligned with the noise peak 92. The first measurement peak 82 may be generated by the noise peak 92. The first measurement peak 82 of the measurement signal 80 may be detected by not the ion 72 but the ultraviolet light 76. The second measurement peak 84 may be detected by the ion 72. Therefore, the ultraviolet light 75 may be detected on the lower electrode 22 more quickly than the ion 72.

Figure 9:
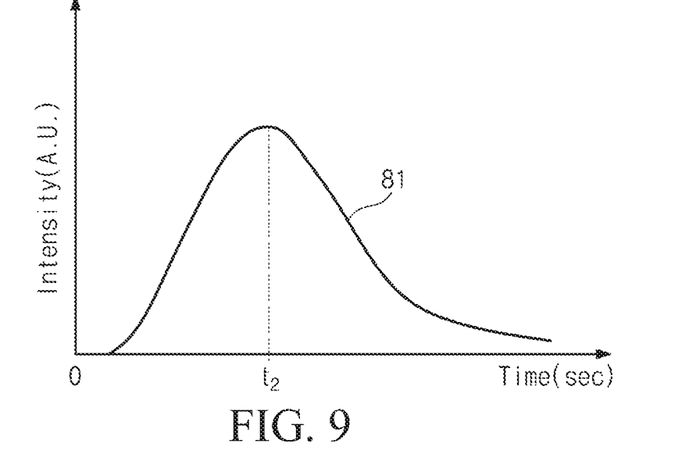
FIG. 9 is a graph illustrating a second measurement peak obtained by removing the first measurement peak aligned with the noise peak of FIG. 8.

FIG. 9 illustrates the second measurement peak 84 obtained by removing the first measurement peak 82 aligned with the noise peak 92 of FIG. 8.

Referring to FIGS. 5 and 9, the control unit 50 removes a part of the measurement signal 80 aligned with the noise signal 90 (S150). According to one example, the control unit 50 removes the first measurement peak 82 aligned with the noise peak 92, and generates a corrected measurement signal 81 with the second measurement peak 84 as a single peak.

Next, the control unit 50 calculates the reference data (S160). According to one example, the second peak time $t_2$ of the second measurement peak 84 may be calculated as the reference data. Thereafter, the control unit 50 may record and/or store the calculated reference data in a database (not shown). Therefore, since the reference data is calculated using the measurement signal 81 corrected by removing a noise, the reference data may have reliability.

When there is no noise of the measurement signal 80 as a result of the determining whether the noise signal 90 exists (S130), the control unit 50 calculates the reference data from a time of a measurement peak (not shown) of the measurement signal 80 (S160). The reference data may include data corresponding to the mobility of the ion 72.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

The invention claimed is:

1. A reference data obtaining method for an ionic mobility measuring apparatus, comprising:
    obtaining a measurement signal by detecting a charge of an ion between electrodes;
    obtaining a noise signal by insulating the electrodes from the ion;
    aligning the noise signal with the measurement signal;
    removing a part of the measurement signal aligned with the noise signal; and
    calculating reference data from a remaining part of the measurement signal.

2. The reference data obtaining method of claim 1, further comprising:
    determining whether a noise of the measurement signal exists according to number of peaks of the measurement signal.

3. The reference data obtaining method of claim 2, wherein, when the number of the peaks of the measurement signal is plural, the noise is determined as being exist, or when the number of the peaks of the measurement signal is singular, the noise is determined as not being exist.

4. The reference data obtaining method of claim 2, wherein the reference data is calculated from times of the peaks of the measurement signal.

5. The reference data obtaining method of claim 1, wherein the measurement signal comprises:
    a first measurement peak having a first peak time; and
    a second measurement peak having a second peak time after the first peak time,
    wherein the noise signal comprises a first noise peak aligned with the first peak time.

6. The reference data obtaining method of claim 5, wherein the calculating the reference data comprises calculating the reference data from a time of the second measurement peak.

7. The reference data obtaining method of claim 5, wherein the removing the part of the measurement signal comprises removing the first measurement peak aligned with the first noise peak.

8. The reference data obtaining method of claim 5, wherein the removing the part of the measurement signal comprises generating a corrected measurement signal having the second measurement peak as a single peak.

9. An apparatus for measuring an ionic mobility of a harmful material, comprising:
- a chamber filled with a harmful material;
- a plurality of electrodes disposed in the chamber;
- a laser configured to irradiate a laser beam to the harmful material between the electrodes;
- a detector connected to the electrodes and detecting an ion of the harmful material ionized by the laser beam; and
- an ion filter disposed between the electrodes and insulating the ion from the electrodes so that the detector detects a noise of the ion through the ion filter.

10. The apparatus of claim 9, wherein the ion filter comprises an ultraviolet transmission filter configured to transmit ultraviolet light generated by collision between the laser beam and the harmful material.

11. The apparatus of claim 10, wherein the ultraviolet transmission filter is disposed between one of the electrodes and the laser beam, and disposed in parallel with the laser beam.

* * * * *